United States Patent [19]

Perret, Jr.

[11] Patent Number: 5,324,348
[45] Date of Patent: Jun. 28, 1994

[54] DISPOSABLE ORTHODONTIC WIRE MARKER

[76] Inventor: Gerard A. Perret, Jr., 14201 Bruce B. Downs Blvd., Suite 2, Tampa, Fla. 33613

[21] Appl. No.: 90,655

[22] Filed: Jul. 13, 1993

[51] Int. Cl.$^5$ .................. C09D 13/00; B43K 19/00
[52] U.S. Cl. .................. 106/19 B; 106/19 E; 106/27 A; 106/27 R; 106/31 R; 401/49
[58] Field of Search .......... 401/49; 106/19 B, 19 E, 106/27 R, 27 A, 31 R

[56] References Cited

U.S. PATENT DOCUMENTS

| | | | |
|---|---|---|---|
| 1,280,580 | 10/1918 | Swett | 424/400 |
| 2,294,403 | 9/1942 | Helmer et al. | 106/19 B |
| 3,068,571 | 12/1962 | Thompson | 433/141 |
| 3,486,912 | 12/1969 | Dyson | 106/31 R |
| 3,491,043 | 1/1970 | Zmitrovis | 106/19 E |
| 3,588,260 | 6/1971 | Caywood et al. | 401/49 |
| 4,052,130 | 10/1977 | Forman | 401/2 |
| 4,198,243 | 4/1980 | Tanaka | 106/19 C |
| 4,741,774 | 5/1988 | Lazar | 106/19 |
| 5,055,498 | 10/1991 | Brachman | 523/164 |
| 5,098,299 | 3/1992 | Fischer | 106/31 R |
| 5,196,237 | 3/1993 | May | 106/27 A |

FOREIGN PATENT DOCUMENTS

| | | | |
|---|---|---|---|
| 62-001767 | 1/1987 | Japan | 106/27 A |
| 4-279684 | 10/1992 | Japan | 106/31 R |

OTHER PUBLICATIONS

Copy of mailing envelope for "Unimarc by Medic Unique" (no date).

*Primary Examiner*—Anthony Green
*Attorney, Agent, or Firm*—Dominik, Stein, Saccocio, Reese, Colitz & Van der Wall

[57] ABSTRACT

A disposable marking device particularly suited for marking wires used in orthodontic treatment is disclosed, comprising a shaft made of metal, plastic, paper, wood, or any other material of suitable stiffness, preferably about the size of a toothpick, coated on at least one end with a pigmented binder, preferably a wax or polymer based material, capable of marking metal wires. A method for marking an orthodontic wire is also disclosed.

13 Claims, No Drawings

DISPOSABLE ORTHODONTIC WIRE MARKER

FIELD OF THE INVENTION

The present invention concerns a marking device, and in particular, a marking device which is particularly suited for marking wires used in orthodontic treatment, and a method for marking an orthodontic wire using the marking device.

DESCRIPTION OF THE RELATED ART

During the course of orthodontic treatment, small brackets are attached to a patient's teeth. Wires with various sizes, shapes, stiffnesses, resiliencies and compositions are then attached to the brackets to apply specific forces to the teeth in order to affect tooth movement. In almost every case, it becomes necessary to place certain bends in precise locations in these wires in order to produce the tooth movements necessary to complete the treatment.

The exact locations at which bends are to be made are determined with the wire in the patient's mouth. In order to properly place bends in an orthodontic wire, the wire must be removed from the patient's mouth. Once the wire is removed from the patient's mouth, the problem then becomes finding those same precise locations at which to make the bends. The most direct method of addressing this problem is to somehow make a mark on the wire in the exact locations of each necessary bend while the wire is still in the mouth. The wire can then be removed from the mouth, and the appropriate bend placed precisely at the marked location.

Products currently on the market and used in the trade for marking intraoral appliances tend to fall into three basic categories: ink markers, crayon markers, and engravers.

Ink markers are readily available in the form of fine point felt tipped marking pens such as those used in addressing labels for packages, making signs or posters, etc. They are typically composed of a non-water-soluble pigment carried in a volatile liquid medium such as butyl alcohol or acetone. When an item is marked, the liquid quickly evaporates, leaving the pigment behind as a mark. The main advantage of this marker is that the mark dries quickly and will not be rubbed off of the wire while removing it from the mouth. A troublesome disadvantage of this type of mark is that an organic solvent must be used to remove the mark from the wire, which further complicates an already intricate process. A further problem is encountered when the appropriate organic solvent is not on hand, in which case the mark is not readily removed from the wire. If marks remain on the front portion of the wire, the patient will have colored marks showing when smiling.

Crayon markers or wax pencils are probably the most common form of marker currently in use. They are composed of a pigmented wax compound, shaped as a long, thin pencil, and wrapped in a paper shell. The paper shell is then peeled back to expose more of the marker as it is used. The main advantage of a wax type of marker is that, unlike the ink marker, it can easily be wiped from the wire with a small gauze or tissue after placement of the bends, thus eliminating any marks that might show when the patient smiles. These markers are also significantly less expensive than the ink markers. The wax material, however, is formulated for application to textured materials such as paper, and, when applied to a non-porous material such as a metal wire, tends to form a "flake" that sits on the wire instead of an actual mark. Upon removal of the wire from the mouth, contact with the cheeks or lips can easily remove one or more flakes, thus requiring replacement of the wire and re-marking.

The engraver type of marker is essentially a pencil shaped, sharply pointed object composed of a hard metal or metal alloy. It marks the wire by cutting a small groove or scratch in the surface. The mark is a permanent mark which cannot be displaced during removal of the wire, and which is practically invisible to the average observer. However, as a result of various properties of metal alloys of which the wires are formed (which are beyond the scope of this discussion), scratching or grooving of a wire significantly weakens the metal. This often leads to breakage of the wire either while placing the necessary bends, or, much worse, after the patient has left the office with the weakened wire in place. For this reason alone, the engraving type of marker is not the marker of choice.

Orthodontists are left with the choice between the ink marker and the wax/crayon marker. Both are useful, and both have established themselves in the trade for years, despite the shortcomings previously discussed.

Dental practitioners have long been concerned with the risk of spread of hepatitis by means of contaminated dental implements. Recently, concern over the risk of spread of Acquired Immune Deficiency Syndrome (AIDS) has heightened these concerns. The Center for Disease Control and most state Dental Practice Acts have all but mandated the sterilization of dental tools. In this respect the ink marker and the wax/crayon marker have an insurmountable flaw: they cannot be sterilized.

Ink markers have a plastic casing that would melt if heat sterilized, not to mention what would happen to the liquid ink at sterilization temperatures. The felt tip mesh, the portion of the marker that actually touches the wire, is not amenable to cold sterilization with chemical solutions. The ink would also bleed into the cold sterilant, and it is possible that the sterilant could filter into the pen.

The disadvantages of putting a wax marker in a heat sterilizer at 270° F. are obvious. Cold sterilization requires soaking of the marker in a liquid solution for a minimum of ten hours. The heavy paper casing may last through a few cycles, but would eventually fall apart. The paper is also a porous material and, as such, is very difficult to disinfect, much less completely sterilize.

Accordingly, each of the types of markers presently available for use in marking orthodontic wires have a number of deficiencies. There remains in the trade a need for a light weight, compact, easy to use marking means which poses no risk of cross-contamination and yet places a mark easily and precisely, which mark does not flake or fall off after marking, is not removed through light contact with soft tissue (e.g. cheeks, lips, tongue), and does not effect the properties of the material being marked, yet is readily removable without special solvents when no longer required.

SUMMARY OF THE INVENTION

The object of the invention is to address the problems discussed above, and to provide a marker which is particularly suited to placing marks on orthodontic wires.

After investigation and experimentation, the present inventor has discovered that all the above-elaborated disadvantages can be overcome by a marking device comprising a small shaft made of metal, plastic, paper, wood, or any other material of suitable stiffness coated on at least one end with a pigmented wax or polymer based material capable of marking metal wires and having properties as discussed below.

A significant feature of the marker of the present invention is that it is constructed of inexpensive materials and is designed to be disposable. Both the conventional ink and wax pencil markers presently available are capable of marking, but they can not be re-used without a risk of cross-contamination of patients.

The marker according to the present invention comprises a disposable shaft with marking material placed on at least one end thereof, with enough marking material to make all of the marks that might be necessary on any one patient. Once the marks are made, the product can be disposed of with other contaminated materials from the procedure. Since the marker cannot be re-used, the risk of cross-contamination is eliminated.

The marker is intentionally designed to be about the size of a toothpick. This provides for easy one-handed dispensing through virtually any toothpick dispenser. Not only does this make the product easily accessible, it also ensures that, once the markers are loaded into the dispenser, the only marker that will be touched is the one about to be used, thus enhancing the product's hygienic qualities.

Accordingly, when considering the advantages of the invention, the marker of the present invention far exceeds any existing product. It is a totally new marker designed to solve the specific problems of ease of transference and adhesion to metallic materials, ease of removal, and elimination of risk of cross-contamination, while having no affect on the properties of the marked material. No product presently on the market satisfies all these requirements.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other marking devices for carrying out the same purposes of the present invention. It should also be realized by those skilled in the art that such equivalent structures do not depart from the spirit and scope of the invention as set forth in the appended claims.

DESCRIPTION OF THE PREFERRED EMBODIMENTS

The shaft of the marker of the present invention is preferably made of wood, but may be made of metal, plastic, paper, or any other material of suitable stiffness sufficient to withstand pressure required to transfer the pigmented material to the item to be marked. The shaft should be lightweight, inexpensive, and able to withstand temperatures at least as high as the melting temperature of the marking material coated onto at least one end of the shaft, and preferably able to withstand approximately 150° F.

The preferred shape of the shaft is rod-shaped with dimensions of 2⅜ inches in length and 1/12th of an inch in diameter. This shape and size will allow convenient dispensing of the marker from conventional toothpick dispensers currently on the market. A particularly preferred shaft material is the material used for forming tooth-picks, and more preferably, a tooth-pick stock material sharpened or pointed at only at the end to be coated. The sharpened or pointed end is then coated with the marking material in order to form a preferred marking device according to the present invention, with the coated end after coating being approximately the same diameter as the body of the shaft, rather than forming a bulbous shape.

However, considering only the purposes of marking, any length that is easily handled is suitable, with a preferred range of about 2½ to 4 inches. The cross-sectional shape is also variable, particularly if dispensing arrangements other than tooth-pick dispensers are made. The cross-section could be square, rectangular, triangular, or any other shape. The thickness can also be varied, though any cross-sectional diameter less than about 1/10th of an inch or greater than 1/15th of an inch may render the marker difficult to handle or dispense from a conventional toothpick dispenser.

Any pigmented, non-toxic, relatively soft wax or polymer based marking material that does not melt or flow at body temperatures will work for the purposes of the present invention. The marking material preferably has sufficient tackiness or stickiness to transfer readily to a wire upon contact therewith and form a mark, yet is sufficiently cohesive as not to cause bonding of the coated tips of the marking devices during normal storage at room temperature. The marking material should have a melting temperature high enough so as to remain stable even if exposed to high temperatures, for example, during shipping. The color of the pigment may be red or black or any color which contrasts with the color of the material to be marked. For use in an orthodontic wire marking means, such a pigment should be safe for contacting with the intra-oral mucosa, and the pigmented wax or polymer should be relatively non-water-soluble, otherwise it might be removed from the wire, or at least moved or altered, simply by contact with saliva or wiping it against a cheek during removal from the patient's mouth.

Examples of suitable materials include crayons from virtually any crayon manufacturer, other wax-based materials with sufficient pigment, soap-based materials with added pigment, and microcrystalline compounds with sufficient pigment and wax-like properties. Considering that only a small amount of marking material is actually transferred from the marking device to the surface to be marked, it should be apparent that the marking material should be sufficiently pigmented so that such a mark is readily visible. The upper limitation on the amount of pigment is dictated by the point at which addition of a greater amount of pigment does not justify the economic cost of the pigment, and/or the point at which the pigment itself exerts an adverse effect on the qualities of the marking composition.

The word "Crayon" is of French origin generic to a variety of marking devices, but has come to be associated in the United States with pigmented mixtures of waxes, fatty acids, colorants, and extenders. Examples of suitable crayon marking compositions include the plastic crayon material described in U.S. Pat. No. 5,055,498 (i.e., a mixture comprising low or medium density polyethylene and at least one of paraffin waxes, microcrystalline waxes, synthetic waxes, vegetable fats and their hydrogenated or sulfonated derivatives, fatty esters of glycols, or fatty acid salts of alkali and alkaline earth metals and aluminum) and the plastic colored crayon material disclosed in U.S. Pat. No. 4,741,744 (i.e., a material comprising wax, coloring matter, ethyl hydroxyethyl cellulose, and a plastic binder such as ethylene-vinyl alcohol copolymer).

A particularly preferred material for the pigment coating is that contained in the "Plastimark Crayon" TM sold by the Dixon Ticonderoga Company, which comprises (with all percentages being in parts by weight, unless otherwise specified):

(1) from 30 to 50%, preferably 37 to 42%, paraffin with a melting point of 130° F. to 150° F., preferably in the range of 138° F. to 140° F., (2) from 5 to 20%, preferably 10 to 15%, synthetic wax, preferably of the Japan substitute consistency, (3) from 5 to 15%, preferably 8 to 12%, microcrystalline wax, (4) from 15 to 30%, preferably 19 to 23%, stearic acid, preferably with a titer of 122° F. to 143° F., (5) from 0 to 8%, preferably 3 to 4%, kaolin clay, (6) from 10 to 20%, preferably 10 to 12%, soap, preferably grated or chipped, and (7) from 0.1 to 5%, preferably 1 to 2%, organic pigment such as Pigment Red 48:1 or Pigment Red 57:1.

However, many other crayon materials and wax materials used in wax pencils and in wax crayon type markers could be selected for the purposes of the present invention on the basis of satisfying the following properties. First, it is highly desirable that the marking material selected should be one which does not flake. This attribute enables the material to stick to the surface of the item being marked much more readily than the other wax type products currently on the market. Since such a material is more adhesive than other products, it is much less likely to be removed from the marked surface by light contact with the patient's soft tissue (cheeks, lips, tongue, etc.). Second, the marking material should be specifically selected as one which is easily removed from non-porous surfaces such as metal wires. A simple firm wiping motion with a cotton gauze o tissue should be all that is required to remove the mark from the marked material. Third, the marking material should in no way alter metallic properties. Finally, the material should be substantially non-water-soluble so as not to be easily removed upon contacting saliva or wiping against the lip or inner cheek.

Crayon materials are well known, and it is within the skill of those working in the art to formulate compositions in order to determine properties of the final product. See, e.g., U.S. Pat. Nos. 2,882,246, 3,933,708 and 4,212,676. The present invention resides not in any particular set of pigmented materials, but in the discovery that particularly formulated materials, when coated on the end of a disposable shaft, will provide a number of advantages not available from any existing marking devices.

Resins used in the marking composition may be crystalline or amorphous polymers or mixtures thereof. Crystalline waxes are well known as the main component for the transfer layer of conventional heat-sensitive recording materials, since the crystalline wax has a definite melting point. Amorphous resins or polymers, i.e., those having no crystalline phase or low crystallinity, include rosin, hydrogenated rosin, rosin ester, copal, chroman-indene resin, polyterpene resin, phenol resin, pinsol, polyamide resin, ketone-aldehyde resin, acrylate derivatives (e.g., methyl methacrylate, polyethyl acrylate, isobutyl methacrylate, butyryl methacrylate), polystyrene, low-molecular weight styrene copolymers (e.g., those having a molecular weight of 20,000 to 25,000) and analogous resins. Further examples of copolymers include ethylenevinyl alcohol and cellulose acetobutyrate. Amorphous waxes include carnauba wax, paraffin wax, bisamide wax, and low molecular weight polyethylene wax. An amorphous polymer is preferred as the dominant phase of the composition as amorphous polymers do not show a definite melting point as compared with a microcrystalline wax or polymer, and thus has properties which only gradually and controllably change over an extended temperature range, as compared to microcrystalline waxes or polymers, which have a rather definite melting point or transition temperature. Mircocrystalline waxes are preferably used as a minor phase of the marking composition.

It is preferred to use amorphous resins or polymers having a fairly low weight average molecular weight (WAMW) of less than 10,000, preferably less than 5,000, or a low molecular weight component. Molecules of low molecular weight generally exhibit increased adhesiveness.

The marking device according to the present invention is produced by a method comprising melting the waxes and/or polymers, uniformly mixing therewith the extenders, modifiers, pigment(s), etc., and dipping the end of the shaft to be coated into the molten composition.

Once the coated marking material has cooled and solidified, the marking device is ready for packaging or use. The device is preferably contained in a dispenser which enables one-handed dispensing, such as a conventional tooth-pick dispenser. The marker can be readily dispensed when needed, used to mark the wire or material to be marked, and disposed. The marking material is preferably sufficiently non-tacky so that the tips of several marking devices will not adhere to each other when stored in contact with each other at room temperature. The melting point of the marking material is preferably 120° F. or greater, more preferably 130° F. or greater.

The suitability of a particular composition can be readily tested for use for marking an orthodontic wire. A composition is tested by coating the end of a shaft as described above, allowing the marking material to cool and solidify, and brushing the coated tip end of the marker against an orthodontic wire. If the mark easily flakes off, or is not readily transferred from the marking device to the orthodontic wire, tackifiers or a low molecular component should be added to the composition. If too much of the material transfers to the orthodontic wire, or the mark is so tacky as to smear easily, solidifiers, plasticizers or extenders should be added to the composition. If the tips of the marking device are tacky or flow at storage temperatures, higher molecular weight (i.e., higher melting) waxes or polymers should be added or used. If the transferred mark is not readily discernable, pigments should be added to the composition. Adjustment of properties is readily made by those working in the art having the above list of desired properties in hand. The invention is thus not limited to any particular binders, although waxes and polymers are preferred in view of biological compatibility and absence of taste or odor, but any binder and pigment combination may be used as long as it satisfies the above-described properties.

Although the marker was first designed for orthodontics, and thus is particularly suited for use in orthodontics, the special properties of the marking material and the disposability of the marker render the marker suitable for use in a number of other medical and scientific applications. Although this invention has been described in its preferred form with a certain degree of particularity with respect to marking orthodontic wires, it is understood that the present disclosure of the preferred form has been made only by way of example and that numerous changes in the details of structures and the composition of the marking material may be resorted to without departing from the spirit and scope of the invention.

Now that the invention has been described,
What is claimed is:

1. A marking device comprising an elongated shaft having a first end and a second end, said first end coated with a marking material comprising a mixture of waxes, fatty acids, and colorants and capable of being transferred in part to a metal surface to form a mark thereon by pressure contact between the marking material and the metal surface, said marking material being substantially non-water-soluble and non-flowing at body temperature.

2. A marking device as in claim 1, wherein said marking material comprises
   from 30 to 50% paraffin wax with a melting point of 130° F. to 150° F.,
   from 5 to 20% synthetic wax,
   from 5 to 15% microcrystalline wax,
   from 15 to 30% stearic acid,
   from 0 to 8%, kaolin clay,
   from 10 to 20% soap, and
   from 0.1 to 5% organic pigment.

3. A marking device as in claim 1, wherein said marking material comprises
   from 37 to 42% paraffin wax with a melting point of 130° F. to 150° F.,
   from 10 to 15% synthetic wax,
   from 8 to 12% microcrystalline wax,
   from 19 to 23% stearic acid,
   from 2% to 4% kaolin clay,
   from 10 to 12% soap, and
   from 1 to 2% organic pigment.

4. A marking device as in claim 1, wherein the marking material is sufficiently tacky to be transferred from the marking device to the surface to be marked without flaking.

5. A marking device as in claim 1, wherein said marking material is sufficiently non-tacky so that the coated marking material of several marking devices will not adhere to each other when stored in contact with each other at room temperature.

6. A marking device as in claim 1, wherein the content of the colorant in the marking material is sufficient to render the material transferred to a receiving surface upon contact therewith readily visible.

7. A marking device as in claim 1, wherein the shaft is rod-shaped with dimensions of approximately 2⅝ inches in length and 1/12th of an inch in diameter.

8. A marking device as in claim 1, wherein the marking material contains a red pigment.

9. A marking device as in claim 1, wherein said first end of said elongated shaft is tapered.

10. A marking device as in claim 1, wherein the melting point of the marking material is 120° F. or greater.

11. A marking device as in claim 1, wherein the melting point of the marking material is 130° F. or greater.

12. A method for marking an orthodontic wire in place in the mouth of a patient, comprising
   forming a marking device comprising an elongated shaft having a first end and a second end, said first end coated with a marking material comprising a mixture of waxes, fatty acids, and colorants and capable of being transferred in part to a metal surface to form a mark thereon by pressure contact between the marking material and the metal surface, said marking material being non-flowing at body temperature, and
   contacting the end of the shaft coated with the marking material against the orthodontic wire at the point to be marked to cause an amount of marking material to be transferred to the wire and form a visible mark thereon.

13. A marking device comprising an elongated shaft having a first end and a second end, said first end coated with a marking material having a melting point of 120° F. or greater and capable of being transferred in part to a metal surface to form a mark thereon by pressure contact between the marking material and the metal surface, said marking material being substantially non-water-soluble and non-flowing at body temperature, said marking material comprising from 30 to 50% paraffin wax with a melting point of 130° F. to 150° F., from 5 to 20% synthetic wax, from 5 to 15% microcrystalline wax, from 15 to 30% stearic acid, from 0 to 8%, kaolin clay, from 10 to 20% soap, and from 0.1 to 5% organic pigment, said marking material being sufficiently tacky to be transferred from the marking device to the surface to be marked without flaking, and wherein the shaft is rod-shaped with dimensions of approximately 2⅝ inches in length and 1/12th of an inch in diameter.

* * * * *